United States Patent [19]

Robl

[11] Patent Number: 5,362,727
[45] Date of Patent: Nov. 8, 1994

[54] SUBSTITUTED AZEPINO[2,1-A]ISOQUINOLINE COMPOUNDS

[75] Inventor: Jeffrey A. Robl, Newtown, Pa.

[73] Assignee: Bristol-Myers Squibb, Princeton, N.J.

[21] Appl. No.: 96,504

[22] Filed: Jul. 26, 1993

[51] Int. Cl.$^5$ .................. A61K 31/55; C07D 487/14; C07D 487/16
[52] U.S. Cl. .................................. 514/214; 540/522
[58] Field of Search ..................... 540/522; 514/214

[56] References Cited

U.S. PATENT DOCUMENTS

| | | | |
|---|---|---|---|
| 4,105,776 | 8/1978 | Ondetti et al. | 424/274 |
| 4,337,201 | 6/1982 | Petrillo | 548/413 |
| 4,339,600 | 7/1982 | Ondetti et al. | 562/426 |
| 4,374,829 | 2/1983 | Harris et al. | 424/177 |
| 4,415,496 | 11/1983 | Harris et al. | 424/258 |
| 4,432,971 | 2/1984 | Karanewsky et al. | 424/177 |
| 4,432,972 | 2/1984 | Karanewsky et al. | 424/177 |
| 4,460,579 | 7/1984 | Karanewsky et al. | 424/200 |
| 4,584,294 | 4/1986 | Ruyle | 514/214 |
| 4,617,301 | 10/1986 | Patchett et al. | 514/214 |
| 4,711,884 | 12/1987 | Karanewsky | 514/226 |
| 4,722,810 | 2/1988 | Delaney et al. | 558/254 |
| 4,749,688 | 6/1988 | Haslanger et al. | 514/19 |
| 4,801,609 | 1/1989 | Haslanger et al. | 514/506 |
| 4,824,832 | 4/1989 | Flynn | 514/214 |
| 4,873,235 | 10/1989 | Parsons et al. | 514/312 |
| 4,879,309 | 11/1989 | Doll et al. | 514/513 |
| 5,061,710 | 10/1991 | Haslanger et al. | 514/266 |
| 5,075,302 | 12/1991 | Neustadt | 514/211 |
| 5,098,934 | 3/1992 | Vevert et al. | 514/513 |
| 5,190,974 | 3/1993 | Clemence et al. | 514/513 |
| 5,208,236 | 5/1993 | Neustadt | 514/237.5 |
| 5,232,920 | 8/1993 | Neustadt | 514/212 |

FOREIGN PATENT DOCUMENTS

| | | |
|---|---|---|
| 481522 | 4/1992 | European Pat. Off. |
| 524553 | 1/1993 | European Pat. Off. |
| 534363 | 3/1993 | European Pat. Off. |
| 534396 | 3/1993 | European Pat. Off. |
| 534492 | 3/1993 | European Pat. Off. |
| 2207351 | 2/1989 | United Kingdom |

OTHER PUBLICATIONS

Smith et al., Biochemistry, vol. 14, pp. 766–771 (1975).
Thorsett, Actual Chim. Ther., vol. 13, pp. 257–268 (1986).

Primary Examiner—Mukund J. Shah
Assistant Examiner—Matthew V. Grumbling
Attorney, Agent, or Firm—Stephen B. Davis

[57] ABSTRACT

Compounds of the formula

[chemical structure showing azepino-isoquinoline ring system with substituents $X_1$, $X_2$, A–NH, and COOR$_3$]

wherein A is $$R_2-S-(CH_2)_n-\underset{R_{12}}{\underset{|}{C}}-\underset{R_1}{\underset{|}{C}}-\quad \text{or}$$

$$R_7OOC-(CH_2)_q-\underset{R_{12}}{\underset{|}{C}}-\underset{R_1}{\underset{|}{C}}-$$

are dual inhibitors of NEP and ACE. Compounds wherein A is $$R_7OOC-\underset{R_1}{\underset{|}{CH}}-\quad \text{or} \quad R_4-\underset{OR_5}{\overset{O}{\underset{||}{P}}}-$$

are selective as ACE inhibitors. Methods of preparation and intermediates are also disclosed.

9 Claims, No Drawings

SUBSTITUTED AZEPINO[2,1-A]ISOQUINOLINE COMPOUNDS

BACKGROUND OF THE INVENTION

Captopril, (S)-1-(3-mercapto-2-methyl-1-oxopropyl)-L-proline, having the structural formula

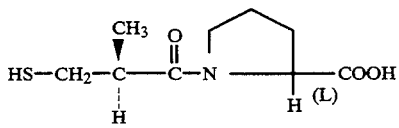

is an orally active angiotensin converting enzyme inhibitor useful for treating hypertension and congestive heart failue. See Ondetti et al. U.S. Pat. No. 4,105,776.

Enalapril, (S)-1-[N-[1-(ethoxycarbonyl)-3-phenylpropyl]-L-alanyl]-L-proline, having the structural formula

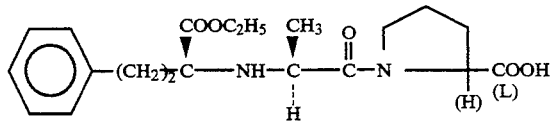

is also an orally active angiotensin converting enzyme inhibitor: Enalapril contains the L-alanyl-L-proline dipeptide. A related compound, lisinopril, also possesses oral angiotensin converting enzyme inhibitor activity and contains the L-lysyl-L-proline dipeptide. See Harris et al. U.S. Pat. No. 4,374,829.

Fosinopril sodium, (4S)-4-cyclohexyl-1-[[(R)-[(S)-1-hydroxy-2-methylpropoxy](4-phenylbutyl)phosphinyl]acetyl]-L-proline propionate (ester), sodium salt having the structural formula

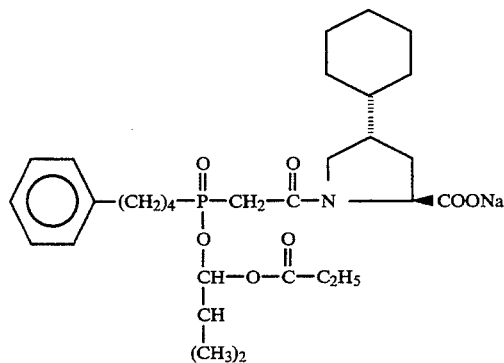

is also an orally active angiotensin converting enzyme inhibitor useful for treating hypertension. See Petrillo U.S. Pat. No. 4,337,201.

Haslanger et al. in U.S. Pat. No. 4,749,688 disclose treating hypertension by administering neutral metalloendopeptidase inhibitors alone or in combination with atrial peptides or angiotensin converting enzyme inhibitors.

Neustadt in U.S. Pat. No. 5,075,302 disclose that mercaptoacyl amino lactams of the formula

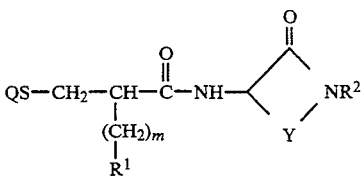

wherein Y includes propylene and butylene, $R^1$ is lower alkyl, aryl or heteroaryl, and $R^2$ is hydrogen, lower alkyl, lower alkoxy lower alkyl, aryl-lower alkyl or heteroaryl-lower alkyl are endopeptidase inhibitors. Neustadt disclose employing such compounds alone or in combination with angiotensin converting enzyme inhibitors to treat cardiovascular diseases such as hypertension, congestive heart failure, edema, and renal insufficiency.

Delaney et al. U.K. Patent 2,207,351 disclose that endopeptidase inhibitors produce diuresis and natriuresis and are useful alone or in combination with angiotensin converting enzyme inhibitors for the reduction of blood pressure. Delaney et al. include various mercapto and acylmercapto amino acids and dipeptides among their endopeptidase inhibiting compounds.

Flynn et al. in European Patent Application 481,522 disclose dual inhibitors of enkephalinase and angiotensin converting enzyme of the formulas

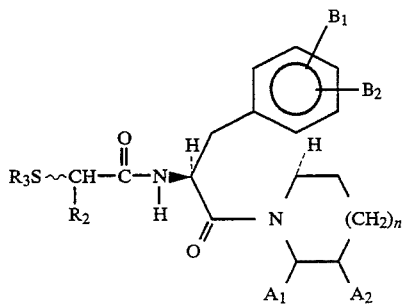

and

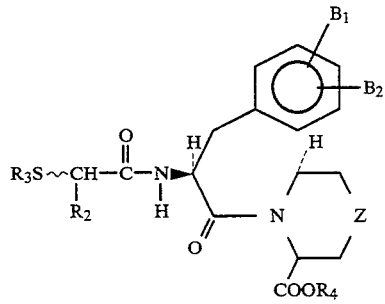

wherein n is zero or one and Z is O, S, $-NR_6-$ or

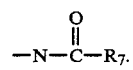

Additional tricyclic dual inhibitors are disclosed by Warshawsky et al. in European Patent Applications 534,363, 534,396 and 534,492.

Karanewsky et al. in U.S. Pat. Nos. 4,432,971 and 4,432,972 disclose phosphonamidate angiotensin converting enzyme inhibitors of the formula

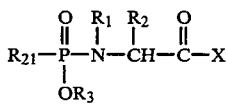

wherein X is a substituted imino or amino acid or ester.

Karanewsky in U.S. Pat. No. 4,460,579 discloses angiotensin converting enzyme inhibitors including those of the formula

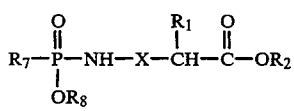

wherein X is a thiazine or thiazepine.

Ruyle in U.S. Pat. No. 4,584,294 disclose angiotensin converting enzyme inhibitors of the formula

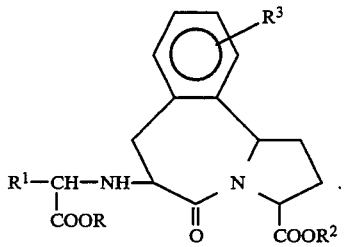

Parsons et al. in U.S. Pat. No. 4,873,235 disclose angiotensin converting enzyme inhibitors of the formula

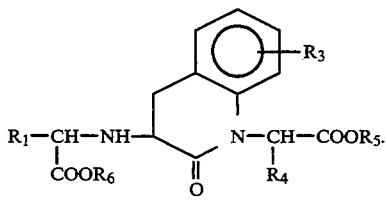

Thorsett, Actual. Chim. Ther., Vol. 13, p. 257–268, (1986) disclose conformationally restricted inhibitors of angiotensin converting enzyme.

SUMMARY OF THE INVENTION

This invention is directed to novel 4-substituted-5-oxo-1H-azepino[2,1-a]isoquinoline-7-carboxylic acids and esters which possess angiotensin converting enzyme inhibition activity and some of which also possess neutral endopeptidase inhibitory activity. This invention is also directed to pharmaceutical compositions containing such selective or dual action inhibitors and the method of using such compositions. This invention is also directed to the process for preparing such novel compounds and novel intermediates.

The novel 4-substituted-5-oxo-1H-azepino[2,1-a]isoquinoline-7-carboxylic acids and esters of this invention include those of the formula

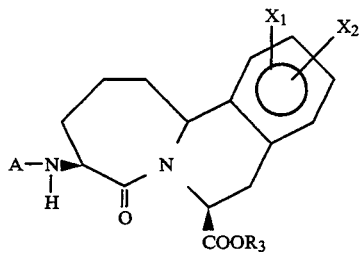

and pharmaceutically acceptable salts thereof wherein:
A is

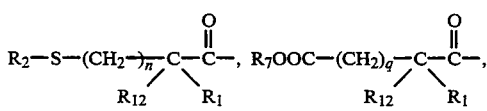

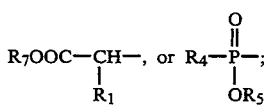

$R_1$ and $R_{12}$ are independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene- or $R_1$ and $R_{12}$ taken together with the carbon to which they are attached complete a cycloalkyl ring or a benzofused cycloalkyl ring;

$R_2$ is hydrogen,

or $R_{11}$—S—;

$R_3$, $R_5$ and $R_7$ are independently selected from hydrogen, alkyl, substituted alkyl, aryl—$(CH_2)_p$—, substituted aryl—$(CH_2)_p$—, heteroaryl—$(CH_2)_p$—,

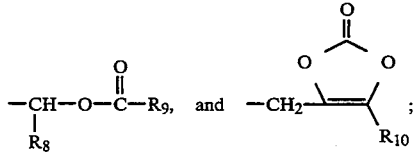

$R_4$ is alkyl, cycloalkyl—$(CH_2)_p$—, substituted alkyl, aryl—$(CH_2)_p$—, substituted aryl—$(CH_2)_p$—, or heteroaryl—$(CH_2)_p$—;

$R_6$ is alkyl, substituted alkyl, cycloalkyl—$(CH_2)_p$—, aryl—$(CH_2)_p$—, substituted aryl—$(CH_2)_p$—, or heteroaryl—$(CH_2)_p$—;

$R_8$ is hydrogen, lower alkyl, cycloalkyl, or phenyl;

$R_9$ is hydrogen, lower alkyl, lower alkoxy, or phenyl;

$R_{10}$ is lower alkyl or aryl—$(CH_2)_p$—;

$R_{11}$ is alkyl, substituted alkyl, cycloalkyl—$(CH_2)_p$—, aryl—$(CH_2)_p$—, substituted aryl—$(CH_2)_p$—, heteroaryl—$(CH_2)_p$—, or —S—$R_{11}$ completes a symmetrical disulfide wherein $R_{11}$ is $$-(CH_2)_n-\underset{R_{12}}{\overset{}{C}}-\underset{R_1}{\overset{O}{\overset{\|}{C}}}-\underset{H}{\overset{}{N}}\text{[azepino-indole with COOR}_3\text{]}$$

$X_1$ and $X_2$ are independently selected from hydrogen, lower alkyl, lower alkoxy, lower alkylthio, halo, trifluoromethyl, hydroxy, amino, —NH(lower alkyl), —N(-lower alkyl)$_2$, cycloalkyl—(CH$_2$)$_p$—, and aryl—(CH$_2$)$_p$—, or $X_1$ and $X_2$ are on adjacent carbons and are joined to complete a benzene ring or are joined to complete —O—(CH$_2$)$_m$—O— wherein m is one or two.

n is zero or one;
p is zero or an integer from 1 to 6; and
q is zero or an integer from 1 to 3.

DETAILED DESCRIPTION OF THE INVENTION

The term "alkyl" refers to straight or branched chain radicals having up to seven carbon atoms. The term "lower alkyl" refers to straight or branched radicals having up to four carbon atoms and is a preferred subgrouping for the term alkyl.

The term "substituted alkyl" refers to such straight or branched chain radicals of 1 to 7 carbons wherein one or more, preferably one, two, or three, hydrogens have been replaced by a hydroxy, amino, cyano, halo, trifluoromethyl, —NH(lower alkyl), —N(lower alkyl)$_2$, lower alkoxy, lower alkylthio, or carboxy.

The terms "lower alkoxy" and "lower alkylthio" refer to such lower alkyl groups as defined above attached to an oxygen or sulfur.

The term "cycloalkyl" refers to saturated rings of 3 to 7 carbon atoms with cyclopentyl and cyclohexyl being most preferred.

The term "alkenyl" refers to straight or branched chain radicals of 3 to 7 carbon atoms having one or two double bonds. Preferred "alkenyl" groups are straight chain radicals of 3 to 5 carbons having one double bond.

The term "substituted alkenyl" refers to such straight or branched radicals of 3 to 7 carbons having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio, or carboxy.

The term "alkylene" refers to straight or branched chain radicals having up to seven carbon atoms, i.e. —CH$_2$—, —(CH$_2$)$_2$—, —(CH$_2$)$_3$—, —(CH$_2$)$_4$—, $$-CH_2-\underset{\underset{CH_3}{|}}{CH}-,\text{ etc.}$$

The term "aryl" refers to phenyl, 1-naphthyl, and 2-naphthyl. The term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), or —N(lower alkyl)$_2$, and di- and tri-substituted phenyl, 1-naphthyl, or 2-naphthyl wherein said substituents are selected from methyl, methoxy, methylthio, halo, hydroxy, and amino.

The term "heteroaryl" refers to unsaturated rings of 5 or 6 atoms containing one or two O and S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl. Also, if the mono or bicyclic ring has an available N-atom such N atom can also be substituted by an N-protecting group such as $$-CH_2-O-CH_2-\text{Ph},\quad -SO_2-\text{Ph}-CH_3,$$

2,4-dinitrophenyl, lower alkyl, benzyl, or benzhydryl.

The compounds of formula I wherein A is $$R_6-\overset{O}{\overset{\|}{C}}-S-(CH_2)_n-\underset{R_{12}}{\overset{}{C}}-\overset{O}{\overset{\|}{C}}-,$$

can be prepared by coupling the acylmercapto containing sidechain of the formula $$R_6-\overset{O}{\overset{\|}{C}}-S-(CH_2)_n-\underset{R_{12}}{\overset{}{C}}-\overset{O}{\overset{\|}{C}}-OH \quad (II)$$

with an azepino[2,1-a]isoquinoline of the formula (III) [structure with H$_2$N, X$_1$, X$_2$, COOR$_3$]

to give the product of the formula

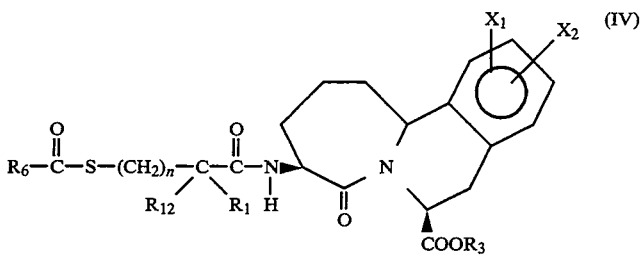

wherein $R_3$ is an easily removable ester protecting group such as methyl, ethyl, t-butyl, or benzyl. The above reaction can be performed in an organic solvent such as methylene chloride and in the presence of a coupling reagent such as 1-ethyl-3-(3-dimethylaminopropyl)carbodiimide, dicylcohexylcarbodiimide, benzotriazol-1-yloxytris(dimethylamino)phosphonium hexafluorophosphate, or carbonyldiimidazole. Alternatively, the acylmercapto carboxylic acid of formula II can be converted to an activated form prior to coupling such as an acid chloride, mixed anhydride, symmetrical anhydride, activated ester, etc.

The product of formula IV can be converted to the mercaptan product of formula I wherein $R_2$ is hydrogen and $R_3$ is hydrogen by methods known in the art. For example, when $R_6$ is methyl and $R_3$ is methyl or ethyl treatment with methanolic sodium hydroxide yields the products wherein $R_2$ and $R_3$ are hydrogen.

The products of formula I wherein $R_2$ is hydrogen can be acylated with an acyl halide of the formula

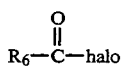

wherein halo is F, Cl or Br or acylated with an anhydride of the formula

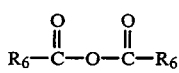

to give other products of formula I wherein $R_2$ is

The products of formula I wherein $R_2$ is $-S-R_{11}$ and $R_{11}$ is alkyl, substituted alkyl, cycloalkyl—$(CH_2)_p$—, aryl—$(CH_2)_p$—, substituted aryl—$(CH_2)_p$—, or heteroaryl—$(CH_2)_p$— can be prepared by reacting the products of formula I wherein $R_2$ is hydrogen with a sulfonyl compound of the formula (VII)

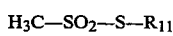

in an aqueous alcohol solvent to yield the desired products. The compounds of formula VII are known in the literature or can be prepared by known methods, see for example, Smith et al., Biochemistry, 14, p 766–771 (1975).

The symmetrical disulfide products of formula I can be prepared by direct oxidation of the product of formula I wherein $R_2$ is hydrogen with iodine as note, for example, Ondetti et al. U.S. Pat. No. 4,105,776.

The acylmercapto sidechain compounds of formula II wherein $R_{12}$ is hydrogen are described in the literature. See, for example, Ondetti et al. U.S. Pat. Nos. 4,105,776 and 4,339,600, Haslanger et al. U.S. Pat. No. 4,801,609, Delaney et al. U.S. Pat. No. 4,722,810, etc.

The acylmercapto sidechain compounds of formula II wherein $R_1$ and $R_{12}$ are both other than hydrogen and n is zero can be prepared by reacting the substituted carboxylic acid of the formula

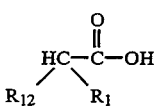

with bis[[(4-methoxy)phenyl]methyldisulfide in the presence of lithium diisopropylamide to give the compound of the formula

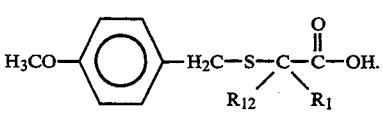

Treatment of the compound of formula IX with strong acid such as trifluoromethanesulfonic acid removes the methoxybenzyl protecting group and is followed by acylation with the acyl halide of formula V or anhydride of formula VI to give the compound of formula II wherein $R_1$ and $R_{12}$ are both other than hydrogen and n is zero.

The acylmercapto sidechain compounds of formula II wherein $R_1$ and $R_{12}$ are both other than hydrogen and n is one can be prepared by reacting the substituted carboxylic acid of the formula

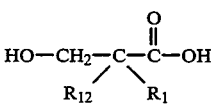

with para-toluenesulfonyl chloride in pyridine to give the lactone of the formula

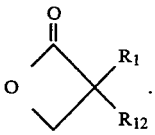

Treatment of the lactone of formula XI with a cesium thioacid of the formula $$\underset{\substack{\parallel \\ Cs-S-C-R_6}}{O} \quad (XII)$$

in the presence of dimethylformamide yields the desired acylmercapto sidechain of formula II wherein $R_1$ and $R_{12}$ are both other than hydrogen and n is one.

The compounds of formula I wherein A is $$R_7OOC-(CH_2)_q\underset{\substack{/ \quad \backslash \\ R_{12} \quad R_1}}{C}-\overset{O}{\underset{\parallel}{C}}-,$$

can be prepared by coupling the acid of the formula $$R_7OOC-(CH_2)_q\underset{\substack{/ \quad \backslash \\ R_{12} \quad R_1}}{C}-\overset{O}{\underset{\parallel}{C}}-OH \quad (XIII)$$

wherein $R_7$ is an ester protecting group with an azepino[2,1-a]isoquinoline of formula III in the presence of a coupling reagent as defined above to give the product of the formula (XIV) [structure with $R_7OOC-(CH_2)_n-C(R_{12})(R_1)-C(=O)-N$ linked to azepinoisoquinoline bearing $X_1, X_2, COOR_3$]

Alternatively, the acid of formula XIII can be converted to an activated form such as an acid chloride prior to the coupling reaction.

The acids of formula XIII are described by Warshawsky et al. in European Patent Application 534,396 and 534,492.

The compounds of formula I wherein A is $$R_7OOC-\underset{R_1}{\overset{|}{CH}}-,$$

can be prepared by reacting a keto acid or ester of the formula $$\underset{\substack{\parallel \quad \parallel \\ R_7O-C-C-R_1}}{O \quad O} \quad (XV)$$

with an azepino[2,1-a]isoquinoline of formulla III under reducing conditions to give the product of the formula (XVI) [structure with $R_7O-C(=O)-CH(R_1)-NH$ linked to azepinoisoquinoline with $X_1, X_2, COOR_3$]

The keto acids and esters of formula XV are described in the literature. See, for example, Ruyle U.S. Pat. No. 4,584,294 and Parsons et al. U.S. Pat. No. 4,873,235.

Alternatively, the azepino[2,1-a]isoquinoline of formula III can be reacted with a triflate of the formula $$\underset{\substack{\parallel \quad | \\ R_7O-C-CH-R_1}}{O \quad OSO_2CF_3} \quad (XVII)$$

to give the product of formula XVI.

The compounds of formula I wherein A is $$R_4-\underset{\substack{\parallel \\ OR_5}}{\overset{O}{P}}-$$

can be prepared by coupling a phosphonochloridate of the formula $$R_4-\underset{\substack{\parallel \\ OR_5}}{\overset{O}{P}}-Cl \quad (XVIII)$$

wherein $R_5$ is lower alkyl or benzyl with an azepino[2,1-a]isoquinoline of formula III. Preferably, the compound of formula III is in its hydrochloride salt form and $R_3$ is lower alkyl or benzyl. The $R_3$ and $R_5$ ester protecting groups can be removed, for example, by hydrogenation to give the corresponding products of formula I wherein $R_3$ and $R_5$ are hydrogen.

The phosphonochloridates of formula XVIII are known in the literature. See, for example, Karanewsky et al. U.S. Pat. Nos. 4,432,971, 4,432,972 and 4,460,579.

The ester products of formula I wherein $R_5$ or $R_7$ is $$-\underset{R_8}{\overset{|}{CH}}-O-\overset{O}{\underset{\parallel}{C}}-R_9 \quad \text{or} \quad -CH_2-\overset{\displaystyle O\underset{\parallel}{\overset{O}{C}}O}{\underset{R_{10}}{\diagdown\diagup}}$$

can be prepared by treating the corresponding compounds of formula I wherein $R_5$ or $R_7$ is hydrogen and $R_3$ is an ester protecting group with a compound of the formula

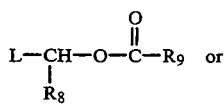
(XIX)

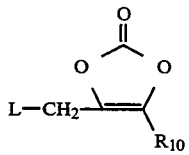
(XX)

wherein L is a leaving group such as chloro, bromo, or tolylsulfonyloxy followed by removal of the $R_3$ ester protecting group.

The ester products of formula I wherein $R_3$ is

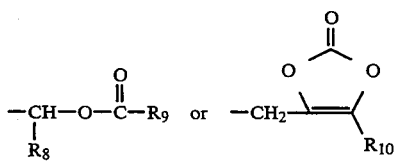

can be prepared by treating the corresponding compounds of formula I wherein $R_3$ is hydrogen and $R_2$ is

with a compound of formula XIX or XX.

The azepino[2,1-a]isoquinolines of formula III can be prepared according to the following process which also forms part of this invention. L-Hydroxynorleucine is converted to the N-protected compound of the formula

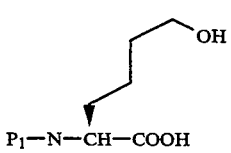
(XXI)

wherein $P_1$ is an amino protecting group such as benzyloxycarbonyl or a group which together with the N-atom forms a protecting group such as phthalimido. For example, treatment with N-carbethoxyphthalimide gives the compound of formula XXI wherein $P_1$—N is

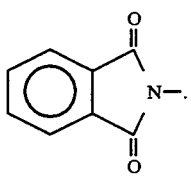

The compound of formula XXI is then coupled with the amino acid ester of the formula

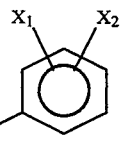
(XXII)

wherein $R_{13}$ is an easily removable ester protecting group such as methyl or ethyl. This coupling reaction is performed in the presence of a coupling reagent such as those listed above and yields the compound of the formula

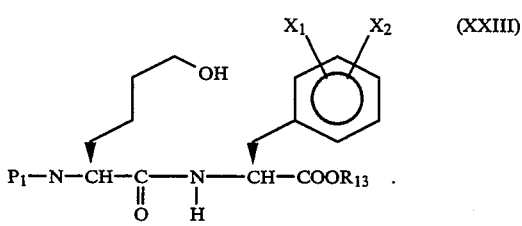
(XXIII)

The alcohol of formula XXIII is oxidized such as by treatment with oxalyl chloride/dimethylsulfoxide and triethylamine to give the aldehyde of the formula

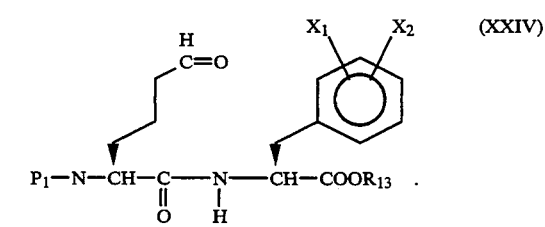
(XXIV)

The aldehyde of formula XXIV can be cyclized by treatment with a non-aqueous acid such as trifluoroacetic acid or p-toluenesulfonic acid in a suitable solvent such as methylene chloride or chloroform to give the oxazolo[3,2-a]azepine-2,5-dione of the formula

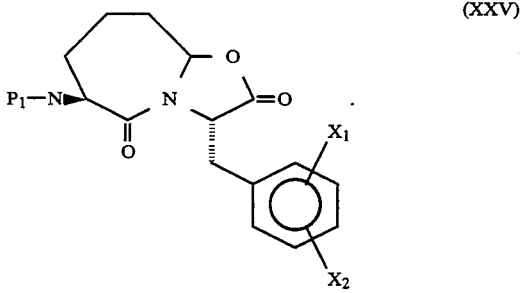
(XXV)

If desired, the aldehyde of formula XXIV can be treated to remove the $R_{13}$ ester protecting group prior to the cyclization reaction.

The compound of formula XXV is treated under strongly acidic conditions such as trifluoromethanesulfonic acid in a suitable solvent such as methylene chloride or chloroform to give the azepino[2,1-a]isoquinoline of the formula

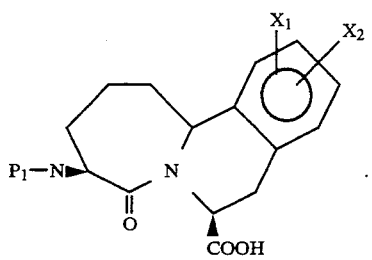

(XXVI)

The compound of formula XXVI is alkylated to introduce the $R_3$ ester protecting group such as by treatment with diazomethane when $R_3$ is methyl followed by treatment to remove the $P_1$ protecting group. For example, when $P_1$—N— is

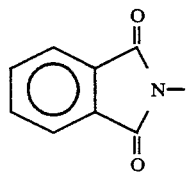

treatment with hydrazine yields the compound of formula III.

In the above reactions if either $X_1$ or $X_2$ or both is hydroxy or amino, the hydroxy or amino substituent would be protected by a known hydroxy or amino protecting group which would be removed as the last step in the synthesis.

The compounds of formula I contain three asymmetric centers in the benzo-fused lactam portion of the structure with an additional center possible in the side chain. While the optically pure form of the azepino[2,1-a]isoquinoline described above is preferred, all such forms are within the scope of this invention. The above described processes can utilize racemates, enantiomers, or diastereomers as starting materials. When diastereomeric compounds are prepared, they can be separated by conventional chromatographic or fractional crystallization methods. Preferably, the hydrogen attached to the bridgehead carbon is in the orientation shown below

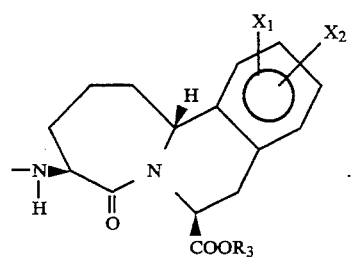

The compounds of formula I wherein $R_3$, $R_5$ and/or $R_7$ are hydrogen can be isolated in the form of a pharmaceutically acceptable salt. Suitable salts for this purpose are alkali metal salts such as sodium and potassium, alkaline earth metal salts such as calcium and magnesium, and salts derived from amino acids such as arginine, lysine, etc. These salts are obtained by reacting the acid form of the compound with an equivalent of base supplying the desired ion in a medium in which the salt precipitates or in aqueous medium and then lyophilizing.

Preferred compounds of this invention are those wherein:

A is

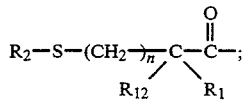

$R_2$ is hydrogen,

or $R_{11}$—S—;
n is zero or one;
$R_{12}$ is hydrogen;
$R_1$ is aryl—$CH_2$—, substituted aryl—$CH_2$—, heteroaryl—$CH_2$—, cycloalkyl—$CH_2$— wherein the cycloalkyl is of 5 to 7 carbons, or straight or branched chain alkyl of 1 to 7 carbons;
$R_6$ is lower alkyl of 1 to 4 carbons or phenyl;
$R_{11}$ is lower alkyl of 1 to 4 carbons;
$R_3$ is hydrogen or lower alkyl of 1 to 4 carbons; and
$X_1$ and $X_2$ are both hydrogen.
Most preferred are the above compounds wherein:
$R_2$ is hydrogen or

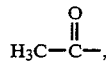

especially hydrogen;
n is zero;
$R_1$ is benzyl; and
$R_3$ is hydrogen.
The compounds of formula I wherein A is

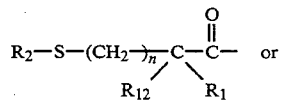

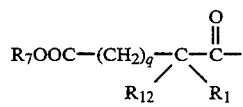

are dual inhibitors possessing the ability to inhibit angiotensin converting enzyme and neutral endopeptidase. The compounds of formula I wherein A is

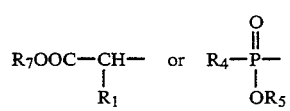

are selective inhibitors possessing the ability to inhibit the angiotensin converting enzyme. Thus, all of the compounds of formula I including their pharmaceutically acceptable salts are useful in the treatment of physiological conditions in which angiotensin converting enzyme inhibitors have been shown to be useful. Such conditions include disease states characterized by abnormalities in blood pressure, intraocular pressure, and renin including cardiovascular diseases particularly hypertension and congestire heart failure, glaucoma, and renal diseases such as renal failure. The dual inhibitors are also useful in the treatment of physiological conditions in which neutral endopeptidase inhibitors have been shown to be useful. Such conditions also include cardiovascular diseases particularly hypertension, hyperaldosteronemia, renal diseases, glaucoma, as well as the relief of acute or chronic pain. Thus, the compounds of formula I are useful in reducing blood pressure and the dual inhibitors of formula I are additionally useful for this purpose due to their diuresis and natriuresis properties. The compounds of formula I including their pharmaceutically acceptable salts can be administered for these effects to a mammalian host such as man at from about 1 mg. to about 100 mg. per kg. of body weight per day, preferably from about 1 mg. to about 50 mg. per kg. of body weight per day. The compounds of formula I are preferably administered orally but parenteral routes such as subcutaneous, intramuscular, and intravenous can also be employed as can topical routes of administration. The daily dose can be administered singly or can be divided into two to four doses administered throughout the day.

The inhibitors of formula I can be administered in combination with human ANF 99-126. Such combination would contain the inhibitor of formula I at from about 1 to about 100 mg. per kg. of body weight and the human ANF 99-126 at from about 0.001 to about 0.1 mg. per kg. of body weight.

The inhibitors of formula I can be administered in combination with other classes of pharmaceutically active compounds. For example, a calcium channel blocker, a potassium channel activator, a cholesterol reducing agent, etc.

The inhibitors of formula I or a pharmaceutically acceptable salt thereof and other pharmaceutically acceptable ingredients can be formulated for the above described pharmacetical uses. Suitable compositions for oral administration include tablets, capsules, and elixirs, and suitable compositions for parenteral administration include sterile solutions and suspensions. Suitable compositions for treating glaucoma also include topical compositions such as solutions, ointments, and solid inserts as described in U.S. Pat. No. 4,442,089. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade. Thin layer chromatography (TLC) was performed in silica gel unless otherwise stated.

EXAMPLE 1

[4S-[4α(R*),7α,12bα]]-1,2,3,4,5,7,8,12-b-Octahydro-4-[(2-mercapto-1-oxo-3-phenylpropyl)amino]-5-oxo-azepino[2,1-a]isoquinoline-7-carboxylic acid a) (S)-2-Phthalimido-6-hydroxyhexanoic acid A solution of (+)-L-ε-hydroxynorleucine [prepared according to the procedure of Bodanszky et al., J. Med Chem., 1978, 21, 1030–1035](1.030 g., 7.0 mmol.) and sodium carbonate (745 mg., 7.0 mmol.) in water (12 mL) was treated with N-carbethoxyphthalimide (1.495 g., 7.0 mmol.) and the mixture was stirred at room temperature for 2 hours. The solution was filtered, cooled to 0° C., and acidified with 6N hydrochloric acid to afford a white precipitate. The solid was collected by filtration and dried in vacuo at 80° C. for 1 hour to give 1.297 g. of the title compound; m.p. 162°-163° C.; $[\alpha]_D = -35.7°$ (c=1.3, methanol).

b) (R*)-N-(2-Phthalimido-6-hydroxy-1-oxohexyl)-L-phenylalanine, ethyl ester

To a solution of L-phenylalanine ethyl ester hydrochloride salt (998 mg., 4.3 mmol) in dimethylformamide (10 mL.) was added with 4-methylmorpholine (575 μl, 529 mg., 5.2 mmol.). After stirring at room temperature for 5 minutes, the solution was cooled to 0° C. and treated successively with (S)-2-phthalimido-6-hydroxyhexanoic acid (1.002 g., 3.6 mmol.), hydroxybenzotriazole (582 mg., 4.3 mmol.) and 1-ethyl-3-(3-dimethylaminopropyl)carbodiimide (770 mg., 4.0 mmol.). The resulting mixture was stirred at 0° C. for 0.5 hour and at room temperature for 1.5 hours. The solution was partitioned between ethyl acetate and water and the organic extract was washed successively with 0.5N hydrochloric acid, water, 50% saturated sodium bicarbonate, and brine, then dried (sodium sulfate), filtered and stripped to give 1.63 g. of essentially pure title product as an oil/foam. TLC (1:1—acetone:hexanes) $R_f=0.30$.

c) (R*)-N-(2-Phthalimido-1,6-dioxohexyl)-L-phenylalanine, ethyl ester

A $-78°$ C. solution of oxalyl chloride (370 μL, 538 mg., 4.2 mmol.) in methylene chloride (10 mL) was treated dropwise with a solution of dry dimethylsulfoxide (610 μL, 672 mg., 8.6 mmol.) in methylene chloride (1.5 mL). After 10 minutes, a solution of the product from part (b) (1.616 g., 3.6 mmol.) in methylene chloride (10 mL) was added. After an additional 15 minutes, the mixture was treated with triethylamine (4.0 mL), stirred at $-78°$ C. for 5 minutes, then let warm to 0° C. The resulting white slurry was partitioned between 0.5N hydrochloric acid and ethyl acetate. The organic extract was washed with brine, then dried (sodium sulfate), filtered and stripped. The residue was flash chromatographed (Merck silica gel, 40:60-acetone:hexanes) to afford 1.474 g. of title product as an oil/foam. TLC (1:1—acetone:hexanes) $R_f=0.45$.

d) [3S-(3α,6β,9aα)]-Tetrahydro-3-(phenylmethyl)-6-phthalimido-oxazolo[3,2-a]azepine-2,5(3H,6H)-dione A mixture of the product from part (c) (6.11 g., 13.6 mmol.) and trifluoroacetic acid (34 mL) in chloroform (205 mL) was refluxed for 6 days. The solution was cooled-to room temperature and neutralized with saturated sodium bicarbonate. The layers were separated and the aqueous layer was extracted with methylene chloride. The pooled organic layers were washed with water, dried (sodium sulfate), filtered and stripped to give a dark yellow-orange oil. The residue was flash chromatographed (Merck silica gel, 40 to 60% ethyl acetate in hexanes) to afford 3,075 g. of the title product as a white foam (92:8 mixture of C-7 diastereomers as determined by NMR). TLC (1:1—ethyl acetate:hexanes) $R_f=0.37$.

e) [4S-(4α,7α,12bα)]-1,2,3,4,5,7,8,12b-Octahydro-4-phthalimido-5-oxo-azepino[2,1-a]isoquinoline-7-carboxylic acid, methyl ester To a slightly chilled (10° C.) solution of trifluoromethanesulfonic acid (20 g) and trifluoromethanesulfonic anhydride (3.0 mL) was added a solution of the product from part (d) (1.50 g., 3.70 mmol) in methylene chloride (50 mL), resulting in a pale-yellow, non-homogeneous mixture. After stirring at room temperature for 21 hours, the solution was poured onto crushed ice and extracted with ethyl acetate. The ethyl acetate extract was washed with water and brine, dried (sodium sulfate), filtered and stripped to give a foam. The foam was dissoved in methanol and methylene chloride and treated with excess ethereal diazomethane for 5 minutes. The excess diazomethane was destroyed by the addition of acetic acid and the solvent was removed on the rotary evaporator to give a solid. The residue was recrystallized from methylene chloride/ethyl acetate-/ethyl ether to afford 880 mg. of pure title product. The mother liquor was flash chromatographed (Merck silica gel, 1:1—ethyl acetate:hexanes) and the desired fractions were stripped and the residue crystallized as above to give an additional 236 mg. of product for a total yield of 1,116 g., m.p. 254°-256° C. TLC (1:1—ethyl acetate:-hexanes) $R_f$=0.25; $[\alpha]_D$=−204.7° (c=0.5, chloroform).

f) [4S-(4α,7α,12bα)]-1,2,3,4,5,7,8,12b-Octahydro-4-amino-5-oxo-azepino[2,1-a]isoquinoline-7-carboxylic acid, methyl ester A solution of the product from part (e) (720 mg., 1.72 mmol.) in methanol (6 mL) was treated with hydrazine monohydrate (184 μL, 190 mg., 3.80 mmol.). After stirring at room temperature for 17 hours, the mixture, now thick with precipitate, was cooled to 0° C and stirred with 10 mL 1N hydrochloric acid for 2 hours. The solution was filtered and the filtrate was washed with ethyl acetate. The ethyl acetate layer was extracted once with 0.5N hydrochloric acid and the pooled aqueous layers were made basic with 1N sodium hydroxide (approximately 13 mL). The aqueous mixture was extracted three times with methylene chloride and the pooled methylene chloride extracts were dried (sodium sulfate), filtered and stripped to give 514 mg. of essentially pure title product as a white oil/foam. TLC (8:1:1—methylene chloride:acetic acid:methanol) $R_f$=0.50.

g) (S)-2-Acetylthio)benzenepropanoic acid

Sodium nitrite (10.3 g., 280 mmol.) was added to a solution of D-phenylalanine (30.0 g., 181 mmol.) and potassium bromide (73.5 g.) in sulfuric acid (2.5N, 365 ml.) over a period of one hour while maintaining the temperature of the reaction mixture at 0° C. The mixture was stirred for an additional hour at 0° C. and then for one hour at room temperature. The reaction solution was extracted with ether, the ether was back extracted with water, and the ether layer was dried over sodium sulfate. Ether was removed in vacuo, and distillation of the oily residue afforded 25.7 g. of (R)-2-bromo-3-benzenepropanoic acid; b.p. 141° (0.55 mm of Hg.); $[\alpha]_D$=+14.5° (c=2.4, chloroform).

A mixture of thioacetic acid (7 ml., 97.9 mmol.) and potassium hydroxide (5.48 g., 97.9 mmol.) in acetonitrile (180.5 ml.) was stirred under argon at room temperature for 1¾ hours. The mixture was cooled in an ice-bath, and a solution of (R)-2-bromo-3-benzenepropanoic acid (20.4 g., 89 mmol.) in acetonitrile (20 ml.) was added over a ten minute period. The reaction was stirred under argon at room temperature for 5 hours, filtered, and the acetonitrile was removed in vacuo. The oily residue was redissolved in ethyl acetate and washed with 10% potassium bisulfate and water. Removal of the ethyl acetate in vacuo afforded 19.6 g. of crude product. The crude product was purified via its dicyclohexylamine salt using isopropyl ether as solvent for crystallization. An analytical sample of (S)-2-(acetylthio)benzenepropanoic acid, dicyclohexylamine salt was prepared by recrystallization from ethyl acetate; m.p. 146°-147°; $[\alpha]_D$=−39.6° (c=1.39, chloroform).

Anal. calc'd. for $C_{11}H_{12}O_3S \cdot C_{12}H_{23}N$: C,68.11; H,8.70; N,3.45; S,7.91 Found: C,67.93; H,8.71; N,3.37; S,7.94.

The free acid was regenerated by suspending the dicyclohexylamine salt in water, acidifying with 1N hydrochloric acid and extracting with ethyl acetate to yield-(S)-2-(acetylthio)benzenepropanoic acid; $[\alpha]_D$=−70.1° (c=1.91, chloroform).

Anal. calc'd. for $C_{11}H_{12}O_3S$: C,58.91; H,5.39; S,14.30 Found: C,58.73; H,5.41; S,14.53.

h) [4S-[4α(R*),7α,12bα]]-1,2,3,4,5,7,8,12b-Octahydro-4-[[2-(acetylthio)-1-oxo-3-phenylpropyl]amino]-5-oxo-azepino[2,1-a]isoquinoline-7-carboxylic acid, methyl ester A cold (0° C.) solution of the product from part (f) (1.72 mmol.) and (S)-2-(acetylthio)benzenepropanoic acid (445 mg., 1.99 mmol.) in methylene chloride (15 mL) was treated with triethylamine (275 μL, 200 mg, 1.98 mmol) followed by benzotriazol-1-yloxy-tris(dimethylamino)phosphonium hexafluorophosphate (838 mg., 1.89 mmol.). The solution was stirred at 0° C. for one hour and then at room temperature for 2 hours. The mixture was partitioned between ethyl acetate and 0.5N hydrochloric acid and washed successively with water and saturated sodium bicarbonate/brine. The solution was dried (sodium sulfate), filtered and stripped. The residue was flash chromatographed (Merck silica gel, 40% to 60% acetone in hexanes) to give 766 mg. of pure title product as a white foam. TLC (1:1—acetone: hexanes) $R_f$=0.39.

i) [4S-[4α(R*),7α,12bα]]-1,2,3,4,5,7,8,12b-Octahydro-4-[(2-mercapto-1-oxo-3-phenylpropyl)amino]-5-oxo-azepino[2,1-a]isoquinoline-7-carboxylic acid A cold (0° C.) solution of the product from part (h) (652 mg., 1.32 mmol.) in methanol (10 mL, deoxygenated via-argon bubbling) was treated with 1N sodium hydroxide (10 mL, deoxygenated via argon bubbling). After stirring for 1 hour, the solution was warmed to room temperature, treated with 5 mL of tetrahydrofuran and stirring was continued for an additional 2 hours. The mixture was acidified with 1N hydrochloric acid and extracted with ethyl acetate. The ethyl acetate extract was washed with water and brine, then dried (sodium sulfate), filtered and stripped to afford an oil. The material was flash chromatographed (Merck silica gel, ethyl acetate followed by 2% acetic acid in ethyl acetate). The desired fractions were pooled, stripped, and azeotroped twice with ethyl acetate. The mixture was dissolved in a small amount of methylene chloride and triturated with hexane to give a foam. The volatiles were stripped, the residue was slurried in hexane, stripped to dryness again, and air dried to give 430 mg. of the title product as a relatively hard white foam. TLC (5% acetic acid in ethyl acetate) $R_f$=0.05; $[\alpha]_D$=−38.7° (c=0.64, chloroform). HPLC: YMC S3 ODS column (6.0×150 mm); eluted with 40% A: 90% water-10% methanol-0.2% phosphoric acid and 60% B: 10% water-90% methanol-0.2% phosphoric acid; flow rate 1.5 mL/min detecting at 220 nm; $t_R$=18.72 min. (100%).

Anal. calc'd. for $C_{24}H_{26}N_2O_4S \cdot 0.32\ H_2O$: C, 64.88; H, 6.04; N, 6.30; S, 7.22 Found: C, 64.88; H, 6.41; N, 5.87; S, 7.09.

EXAMPLE 2

1000 tablets each containing the following ingredients:

| | |
|---|---|
| 4S-[4α(R*),7α,12bα]]-1,2,3,4,5,7,8,12b-Octahydro-[(2-mercapto-1-oxo-3-phenylpropyl)amino]-5-oxo-azepino[2,1-a]isoquinoline-7-carboxylic acid | 200 mg. |
| Cornstarch | 100 mg. |
| Gelatin | 20 mg. |
| Avicel (microcrystalline cellulose) | 50 mg. |
| Magnesium stearate | 5 mg. |
| | 375 mg. | are prepared from sufficient bulk quantities by mixing the product of Example 1 and cornstarch with an aqueous solution of the gelatin. The mixture is dried and ground to a fine powder. The Avicel and then the magnesium stearate are admixed with granulation. The mixture is then compressed in a tablet press to form 1000 tablets each containing 200 mg. of active ingredient.

Similar procedures can be employed to form tablets or capsules containing from 50 mg. to 500 mg. of active ingredient.

What is claimed is:

1. A compound of the formula

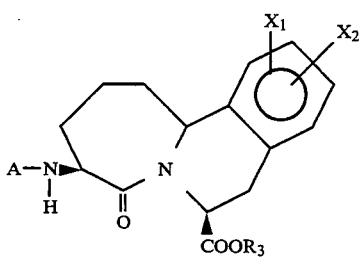

including a pharmaceutically acceptable salt thereof wherein:

A is

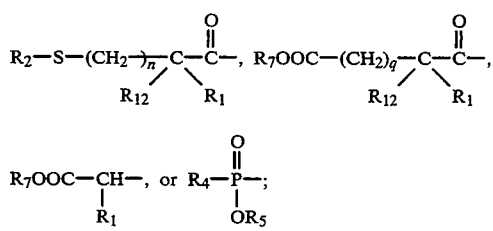

$R_1$ and $R_{12}$ are independently selected from the group consisting of hydrogen, alkyl, alkenyl, cycloalkyl, substituted alkyl, substituted alkenyl, aryl, substituted aryl, heteroaryl, cycloalkyl- alkylene-, aryl-alkylene-, substituted aryl-alkylene-, and heteroaryl-alkylene- or $R_1$ and $R_{12}$ taken together with the carbon to which they are attached complete a cycloalkyl ring or a benzofused cycloalkyl ring;

$R_2$ is hydrogen,

or $R_{11}$—S—;

$R_3$, $R_5$ and $R_7$ are independently selected from the group consisting of hydrogen, alkyl, substituted alkyl, aryl—$(CH_2)_p$—, substituted aryl —$(CH_2)_p$—, heteroaryl—$(CH_2)_p$—,

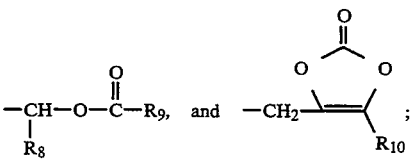

$R_4$ is alkyl, cycloalkyl—$(CH_2)_p$—, substituted alkyl, aryl—$(CH_2)_p$—, substituted aryl—$(CH_2)_p$—, or heteroaryl—$(CH_2)_p$—;

$R_6$ is alkyl, substituted alkyl, cycloalkyl—$(CH_2)_p$—, aryl—$(CH_2)_p$—, substituted aryl—$(CH_2)_p$—, or heteroaryl—$(CH_2)_p$—;

$R_8$ is hydrogen, lower alkyl, cycloalkyl, or phenyl;
$R_9$ is hydrogen, lower alkyl, lower alkoxy, or phenyl;
$R_{10}$ is lower alkyl or aryl—$(CH_2)_p$—;
$R_{11}$ is alkyl, substituted alkyl, cycloalkyl—$(CH_2)_p$—, aryl—$(CH_2)_p$—, substituted aryl—$(CH_2)_p$—, heteroaryl—$(CH_2)_p$—, or —S—$R_{11}$ completes a symmetrical disulfide wherein $R_{11}$ is

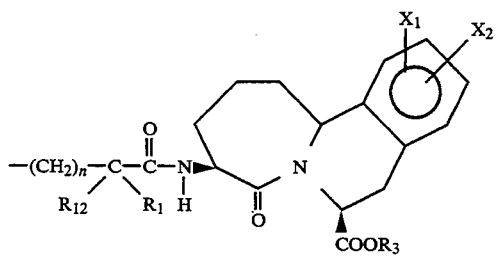

$X_1$ and $X_2$ are independently selected from the group consisting of hydrogen, lower alkyl, lower alkoxy, lower alkylthio, halo, trifluoromethyl, hydroxy, amino, —NH(lower alkyl), —N(lower alkyl)$_2$, cycloalkyl—$(CH_2)_p$—, and aryl—$(CH_2)_p$—, or $X_1$ and $X_2$ are on adjacent carbons and are joined to complete a benzene ring or are joined to complete —O—$(CH_2)_m$—O— wherein m is one or two;
n is zero or one;
p is zero or an integer from 1 to 6; and
q is zero or an integer from 1 to 3.

2. A compound of claim 1 wherein:
A is

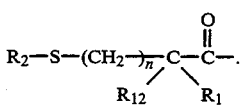

3. A compound of claim 2 wherein:
$R_2$ is hydrogen,

or $R_{11}$—S—;
$R_3$ is hydrogen or lower alkyl of 1 to 4 carbons;
n is zero or one;
$R_{12}$ is hydrogen;

$R_{11}$ is lower alkyl or 1 to 4 carbons;

$R_1$ is aryl—$CH_2$—, substituted aryl—$CH_2$—, heteroaryl—$CH_2$—, cycloalkyl—$CH_2$— wherein cycloalkyl is of 5 to 7 carbons, or straight or branched chain alkyl of 1 to 7 carbons;

$R_6$ is lower alkyl of 1 to 4 carbons or phenyl; and $X_1$ and $X_2$ are both hydrogen.

4. A compound of claim 3 wherein:

$R_2$ is hydrogen or

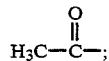

n is zero;

$R_1$ is benzyl; and $R_3$ is hydrogen.

5. The compound of claim 4, [4S-[4α(R*),7α,12bα]]-1,2,3,4,5,7,8,12b-octahydro-4-[(2-mercapto-1-oxo-3-phenylpropyl)amino]-5-oxo-azepino[2,1a]isoquinoline-7-carboxylic acid.

6. A pharmaceutical composition useful in the treatment of cardiovascular disease such as hypertension and congestive heart failure comprising a pharmaceutically acceptable carrier and one or more compounds of the formula

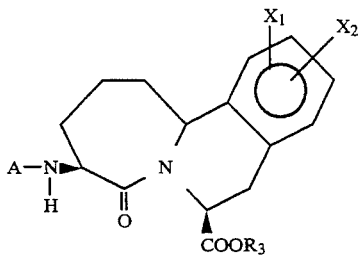

including a pharmaceutically acceptable salt thereof wherein A, $X_1$, $X_2$, and $R_3$ are as defined in claim 1.

7. A method of treating cardiovascular diseases such as hypertension and congestive heart failure in a mammalian species which comprises administering an effective amount of the composition of claim 6.

8. A compound of the formula

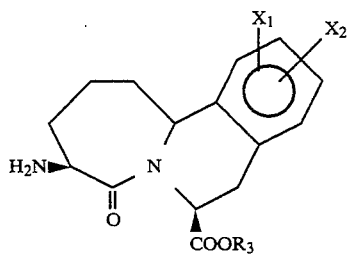

wherein $X_1$ and $X_2$ are independently selected from the group consisting of hydrogen, lower alkyl, lower alkoxy, lower alkylthio, halo, trifluoromethyl, hydroxy, amino, —NH(lower alkyl), —N(lower alkyl)$_2$, cycloalkyl—$(CH_2)_p$—, and aryl—$(CH_2)_p$—, or $X_1$ and $X_2$ are on adjacent carbons and are joined to complete a benzene ring or are joined to complete —O—$(CH_2)_m$—O— wherein m is one or two;

$R_3$ is hydrogen, lower alkyl, or aryl—$(CH_2)_p$—; and p is zero or an integer from 1 to 6.

9. The compound of claim 8 wherein:
$X_1$ and $X_2$ are both hydrogen; and
$R_3$ is methyl.

* * * * *